(12) United States Patent
Yu (10) Patent No.: US 6,306,200 B1
(45) Date of Patent: Oct. 23, 2001

(54) HAND-HELD MULTIPLE SYSTEM GAS CHROMATOGRAPH

(75) Inventor: Conrad M. Yu, Antioch, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/441,902

(22) Filed: Nov. 17, 1999

(51) Int. Cl.$^7$ ................................................. B01D 15/08
(52) U.S. Cl. ............................. 96/102; 96/104; 96/105; 73/23.36
(58) Field of Search .................. 95/82–89; 96/101–107; 73/23.35, 23.36, 23.39

(56) References Cited

U.S. PATENT DOCUMENTS

| | | | |
|---|---|---|---|
| 4,038,055 | * | 7/1977 | Varano et al. ........................... 96/102 |
| 4,935,040 | * | 6/1990 | Goedert ................................. 96/104 X |
| 5,092,155 | * | 3/1992 | Rounbehler et al. ................ 96/107 X |
| 5,092,218 | * | 3/1992 | Fine et al. ............................... 95/82 X |
| 5,147,538 | * | 9/1992 | Wright et al. ........................ 96/101 X |
| 5,236,668 | * | 8/1993 | Higdon ................................. 96/104 X |
| 5,492,555 | * | 2/1996 | Strunk et al. ........................ 96/105 X |
| 5,611,846 | * | 3/1997 | Overton et al. .......................... 96/102 |
| 5,720,798 | * | 2/1998 | Nickerson et al. ..................... 96/102 |
| 5,804,701 | * | 9/1998 | Berger ................................. 96/105 X |
| 5,846,292 | * | 12/1998 | Overton .............................. 96/102 X |

OTHER PUBLICATIONS

UCRL–JC–130439, "A High Performance Hand–Held Gas Chromatograph", Conrad M. Yu, Micro–Electro–Mechanical–System Sysmposium, Nov. 1998.

* cited by examiner

*Primary Examiner*—Robert H. Spitzer
(74) *Attorney, Agent, or Firm*—L. E. Carnahan; Alan H. Thompson (57) ABSTRACT

A multiple parallel hand-held gas chromatograph (GC) system which includes several independent GCs. Each independent GC has its own injector, separation column, detector and oven and the GCs are mounted in a light weight hand-held assembly. Each GC operates independently and simultaneously. Because of different coatings in different separation columns, different retention times for the same gas will be measured. Thus, for a GC system with multiple parallel GCs, the system can measure, in a short period, different retention times and provide a cross-reference in the determination of the measured gas and to become a two-dimensional system for direct field use.

19 Claims, 6 Drawing Sheets

HAND-HELD MULTIPLE SYSTEM GAS CHROMATOGRAPH

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to gas chromatography, particularly to portable gas chromatograph systems and more particularly to a multiple parallel hand held gas chromatograph (GC) system wherein each independent GC unit within the system has its own injector, separation column, detector and oven retained in a light weight compartment.

Gas chromatography (GC) has proven to be a reliable method for identifying unknown chemical mixtures. In a GC, an unknown chemical mixture is first injected and carried by a carrier gas into its separation column. In the separation column, the chemical mixture is distributed between two phases, one a mobile phase and the other the stationary phase. The mobile phase is transported by a carrier gas in the separation column, and the stationary phase is adsorbed into a solid from the flowing mobile phase. Based upon the kinetics of the adsorption-desorption process in the gas-solid interface in the column, different chemicals achieve different moving speeds in the carrier gas. Within a precise column length, the chemical mixture can be separated into various components and recorded by the detector. For the conventional GC, detector sensitivities are at about parts per million for thermal sensitivity detectors and parts per billion for various ion cell detectors. Chemical components are identified through their retention times—the traverse time for each of them as they pass through the separation column.

The separation efficiency of the GC column is related to the degree to which a solute band broadens (which is a function of the width of the peak, w) relative to the length of time the band requires to traverse the column (its retention time $t_R$). The number of theoretical plates N is defined as, $$N=16(t_R/W)^2 \tag{1}$$

Or, the number of effective theoretical plates is defined as, $$N=5.56[(t_R-t_M)/w_{1/2}] \tag{2}$$

where $t_M$ is the duration for nonabsorbed gases to traverse the separation column and $w_{1/2+1}$ the half linewidth of a signal peak. The efficiency of a separation column is measured by the number of theoretical plates per unit length or the "height equivalent to a theoretical plate" h (HETP), $$h=L/n \tag{3}$$

Or, the "height equivalent to one effective theoretical plate" H (HEETP), $$H=L/N \tag{4}$$

In the conventional GC, the separation column is usually formed by a glass capillary with a diameter ranging from 150 to 300 microns and a length of around 100 meters. The values of h or H are on the order of millimeters. To achieve this high column efficiency, the temperature of the separation column needs to be uniform. It must be placed in a large, well-insulated oven. Because of this, conventional GCs are bulky, have high power consumption, and are slow in response.

Recently, efforts have been directed to developing portable GCs for field operations, even miniaturized to a hand-held size.

Performance requirements on field portable GCs are more stringent than those for laboratory GCs. Not only do instruments need to be smaller, more rugged, and consume low power, they also need to be a higher speed for analysis. In the conventional GC, the determination of the separated gas is by its retention time. Some gases may have quite similar retention times in a particular coated separation column, but not in other coated separation columns. Thus, there are normally two or more exchangeable separation columns in each conventional GC. These exchangeable separation columns share a common injector, oven, and monitoring system. Thus, it takes a considerable period of time to change from one separation column to another especially if the temperature of the oven is quite different.

The hand-held GC has a wide appeal for numerous applications, such as toxic gas monitors, pollution detectors, reaction gas analysis, and law enforcement usage. To miniaturize a conventional GC, one first must first miniaturize its separation column and oven assembly.

The separation column and oven assembly can be greatly simplified when make from a highly thermal conductive material. Silicon has higher thermal conductivity than glass, and its surface under ambient conditions will naturally form silicon dioxide, an inert material which is ideal for forming the inner liner of the separation column. To form a highly efficient separation column on a silicon wafer, the column must have (a) a circular cross section, (b) an extremely smooth inner surface, and (c) proper diameter in terms of its length. The heater can then be made directly on the same silicon wafers or on a separate one. Such a hand-held GC is described in UCRL-JC-130439 "A High Performance Hand-Held Gas Chromatograph," Conrad M. Yu, November 1998.

Because of the small sample size, the thermal conductivity detector needs to be extremely sensitive. The heat capacity of the heater and the total amount of conductive heat loss other than that due to the carrier gas has to be minimized. This device is small so it can allow for the direct interconnecting of the thermal detector into the gas stream. All this is done by MEMS (Micro-Electro-Mechanical-System) technology.

Fabrication of a miniaturized separation column using MEMS wafer alignment and bonding, column coating and conditioning, fabrication of a miniaturized thermal conductivity detector using MEMS, assembly of the main components, the sample injector, the capillary column, and the detector and related electronics, as well as test results, for a miniature silicon GC is described in above-referenced UCRL-JC-130439; and such is incorporated herein by reference thereto.

The present invention involves a hand-held multiple parallel gas chromatograph (GC) system which includes several independent GC units each having its own injector, separation column, detector, and oven, mounted in a light weight housing. Each GC unit operates independently and simultaneously. Different retention times for the same gas may be measured because of different coatings in the different separation columns. The multiple parallel GC system of the present invention is constructed utilizing MEMS technology, which enables miniaturization of various components of the system.

SUMMARY OF THE INVENTION

It is an object of the present invention to provide a hand-held gas chromatograph for direct field use.

A further object of the invention is to provide a hand-held multiple system gas chromatograph.

A further object of the invention is to provide a multiple parallel, hand-held gas chromatograph system which includes several independent gas chromatographs.

Another object of the invention is to provide a hand-held gas chromatograph system having multiple parallel independent gas chromatographs each having its own injector, separation column, detector, and oven.

Another object of the invention is to provide a small, hand-held gas chromatograph system mounted in a light weight carrier, where the system comprises multiple independent gas chromatographs, each having the capability to operate independently and simultaneously.

Another object of the invention is to provide a gas chromatograph system having multiple independent gas chromatographs with different separation columns having different coatings, whereby different retention times for the same gas can be measured.

Another object of the invention is to provide a hand-held gas chromatograph system with multiple, parallel, independent gas chromatographs which can measure, in a short time period, different retention times and provide a cross-reference in the determination of the measured gas and to provide a two-dimensional system for direct field use.

Other objects and advantages of the present invention will become apparent from the following description and accompanying drawings. The present invention is a hand-held gas chromatograph (GC) system having multiple parallel independent GCs. Each independent GC has its own injector, separation column, detector and oven; and the GCs are mounted in a light weight carrier or housing. Thus, the GC system may be effectively utilized for detection of various chemicals and biological substances in the field. Due to the individual GCs having their own silicon separation column and a compact-size oven, the major volume in the carrier is occupied by other hardware. Thus, in the same volume carrier, multiple independent complete GCs with a different coated separation column for each GC can be installed. Since the independent GCs are operated simultaneous, with different coated separation columns, they provide different retention times for the same chemical compound. This feature not only provides more versatility but also provides a second dimension in its selectivity.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

The present invention is directed to a compact size, hand-held gas chromatograph (GC) system having multiple independent GCs within the same carrier. A unique feature of the hand-held GC system of the present invention is its silicon separation column and its compact size oven, and wherein each of the multiple parallel GCs has it own injector, separation column, detector and oven. In addition the power consumption of the GC system is low. Each of the multiple independent GCs may be operated simultaneously. Because of different coatings in different separation columns, different retention times for the same gas will be measured. Because of the compact size of the multiple GCs and their ovens, a major of the volume of the hand-held carrier is occupied by other hardware, therefore, in the same volume multiple independent complete GCs with different coated separation columns can be effectively mounted in the carrier. Since the multiple, independent GCs can be operated simultaneously, the different GC with the different coated separation column will provide different retention times for the same chemical compound. This feature not only provides the GC system of the present invention with greater versatility, but also provides a second dimension in its selectively. Thus, the invention effectively and efficiently enables detection of various chemical and biological substances in the field.

Figure 1:
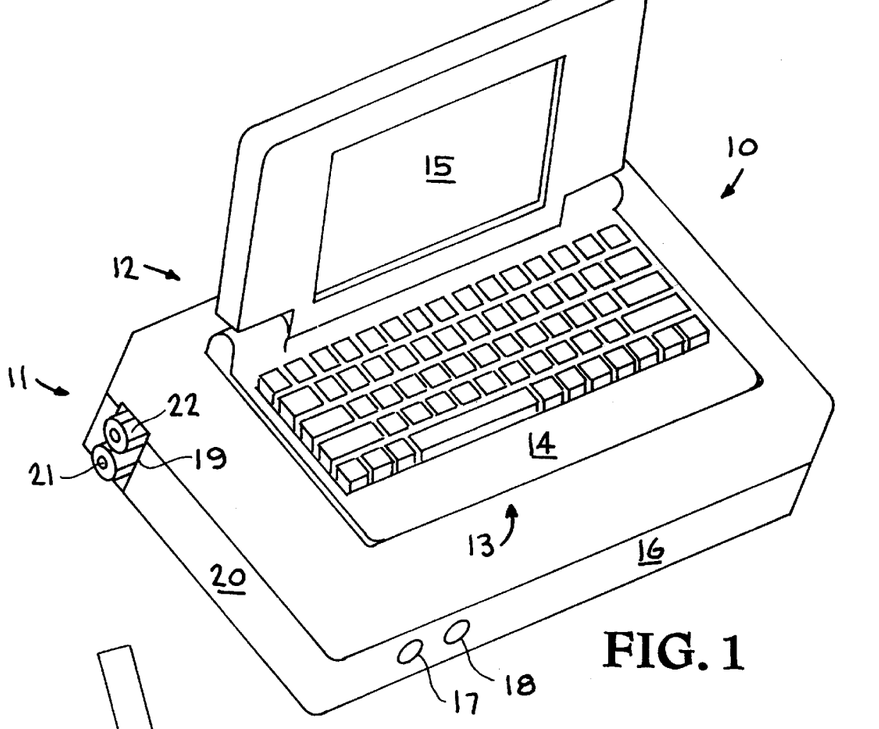
FIG. 1 is a perspective view of an embodiment of a hand-held carrier containing a multiple system gas chromatograph (GC) made in accordance with the present invention.
Figure 2:
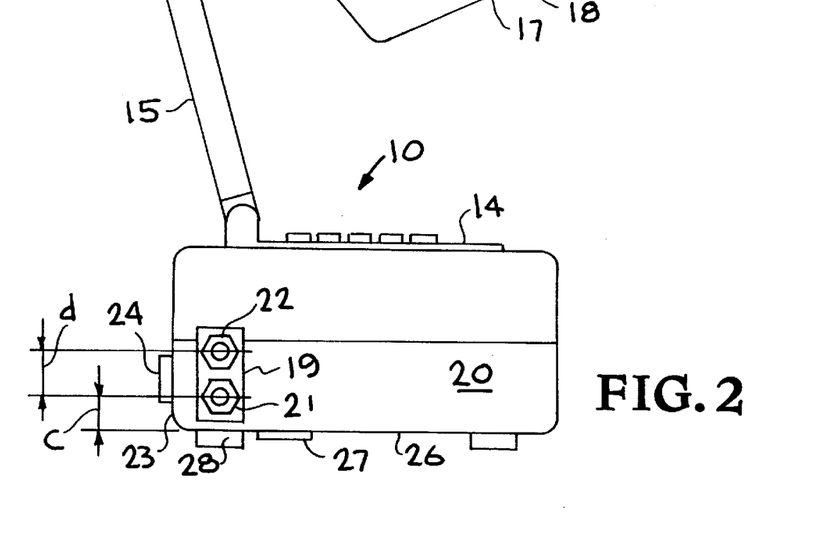
FIG. 2 is a side view of the hand-held GC carrier of FIG. 1 showing side, rear, and bottom connectors.
Figure 3:
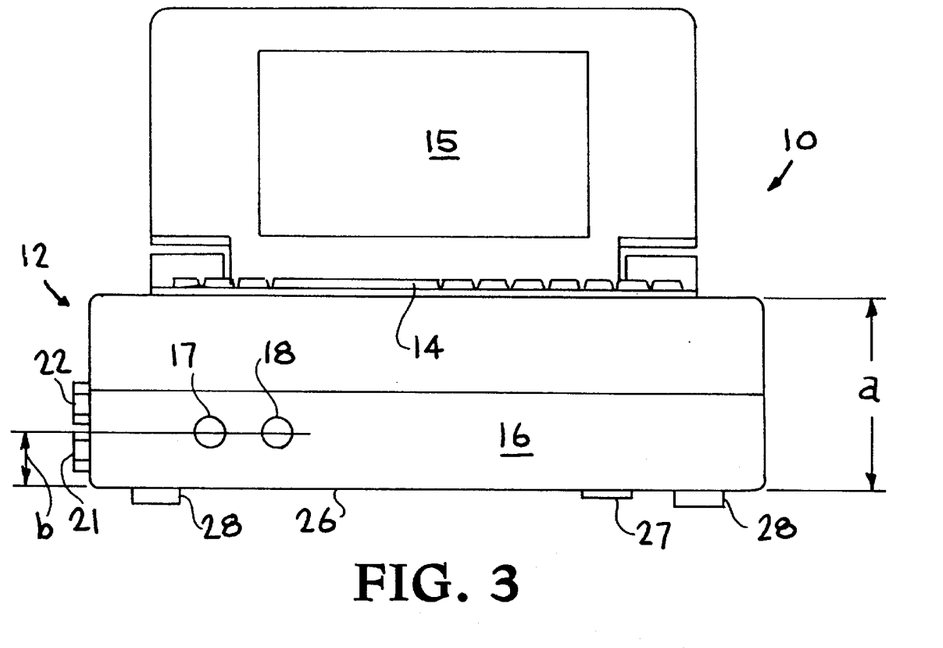
FIG. 3 is a front view of the hand-held GC carrier of FIG. 1 showing front, side, and bottom connectors.
Figure 4:
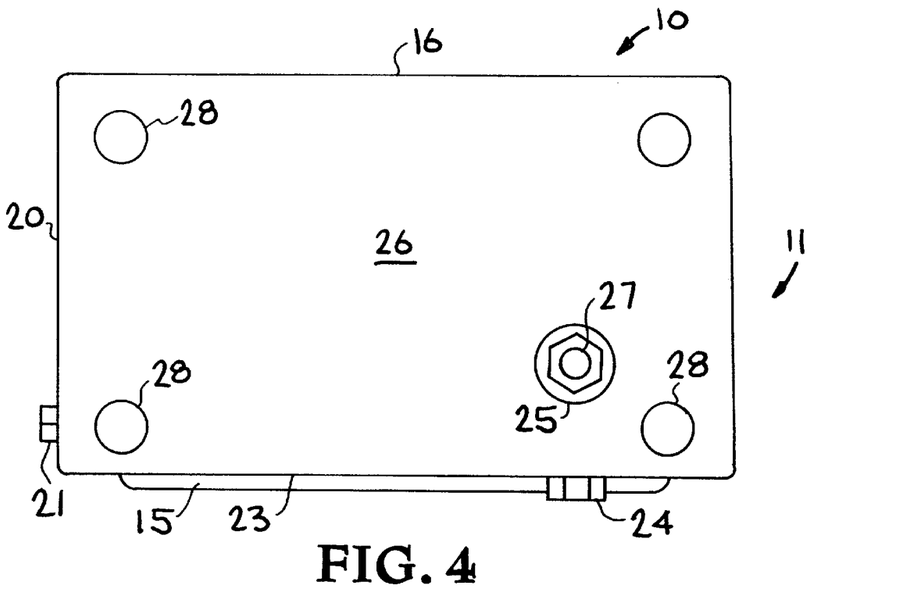
FIG. 4 is a bottom view of the hand-held GC carrier of FIG. 1 showing bottom, side and rear connectors.

Referring now to the drawings FIGS. 1–4 illustrate an embodiment of a hand-held carrier for the multiple system gas chromatograph of the present invention. The hand-held carrier, housing, or case is indicated generally at 10 and comprises a lower carrier section 11 and an upper carrier section 12 which are interconnected by connectors such as screws or bolts, not shown. The lower carrier section 11 contains the components of the GC and the upper carrier sections contain a lap-top type computer generally indicated at 13 which includes a keyboard 14 and a screen or monitor 15. Lower carrier section 11 as seen in FIG. 1 in a front wall section 16 is provided with a pair of openings or holes 17 and 18, and an opening 19 in a side wall section 20 for a pair of connectors 21 and 22. As seen in FIG. 2, the lower carrier section 11 is provided with an opening, not shown, (see FIG. 5) in a rear wall section 23 in which a connector 24 is located, and an opening 25 (see FIG. 4) in a bottom section 26 in which a connector 27 is located. The openings 17 and 18, connectors 21 and 22, and connector 27 are seen in FIG. 3, while FIG. 4, in addition to opening 25 and connector 27 in bottom section 26 illustrates connector 24 in rear section 23 and connector 21 in side section 20. Also, lower carrier section 11 is provided with a plurality of support pads 28 (4 shown).

By way of example, the carrier 10 (sections 11 and 12) has a height of 2.950 inches as indicated by arrow a in FIG. 3, with the center of openings 17 and 18 being 0.840 inch from the bottom section 26 as indicated by arrow b, with the center of connector 21 being 0.548 inch from bottom section 26 as indicated by arrow c in FIG. 2, with the centers of connectors 21 and 22 being separated 0.712 inch as indicated by arrow d.

Figure 5:
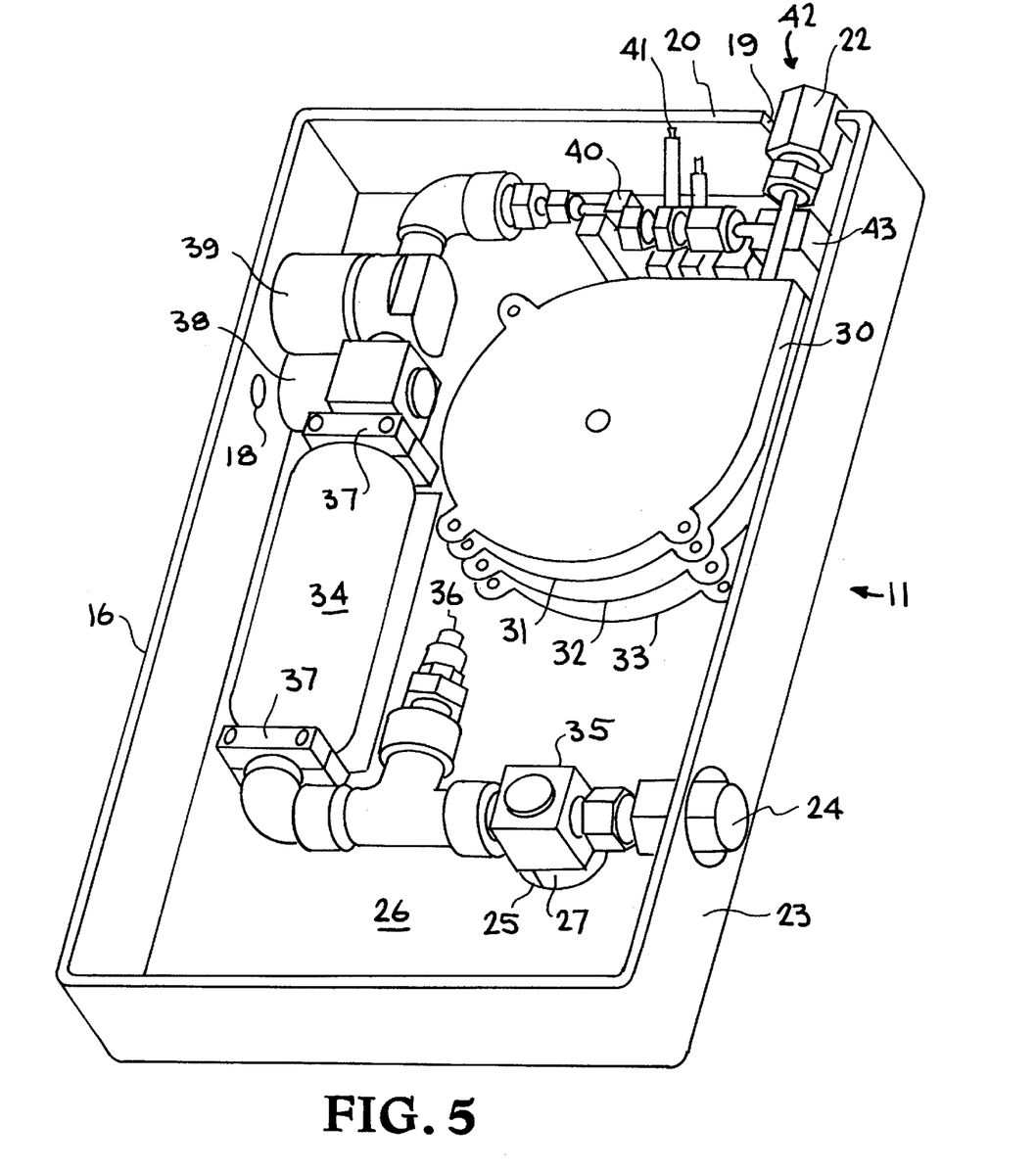
FIG. 5 is a perspective view of an embodiment of a lower section of a hand-held carrier, similar to FIG. 1, illustrating multiple GCs and associated equipment mounted therein.
Figure 6:
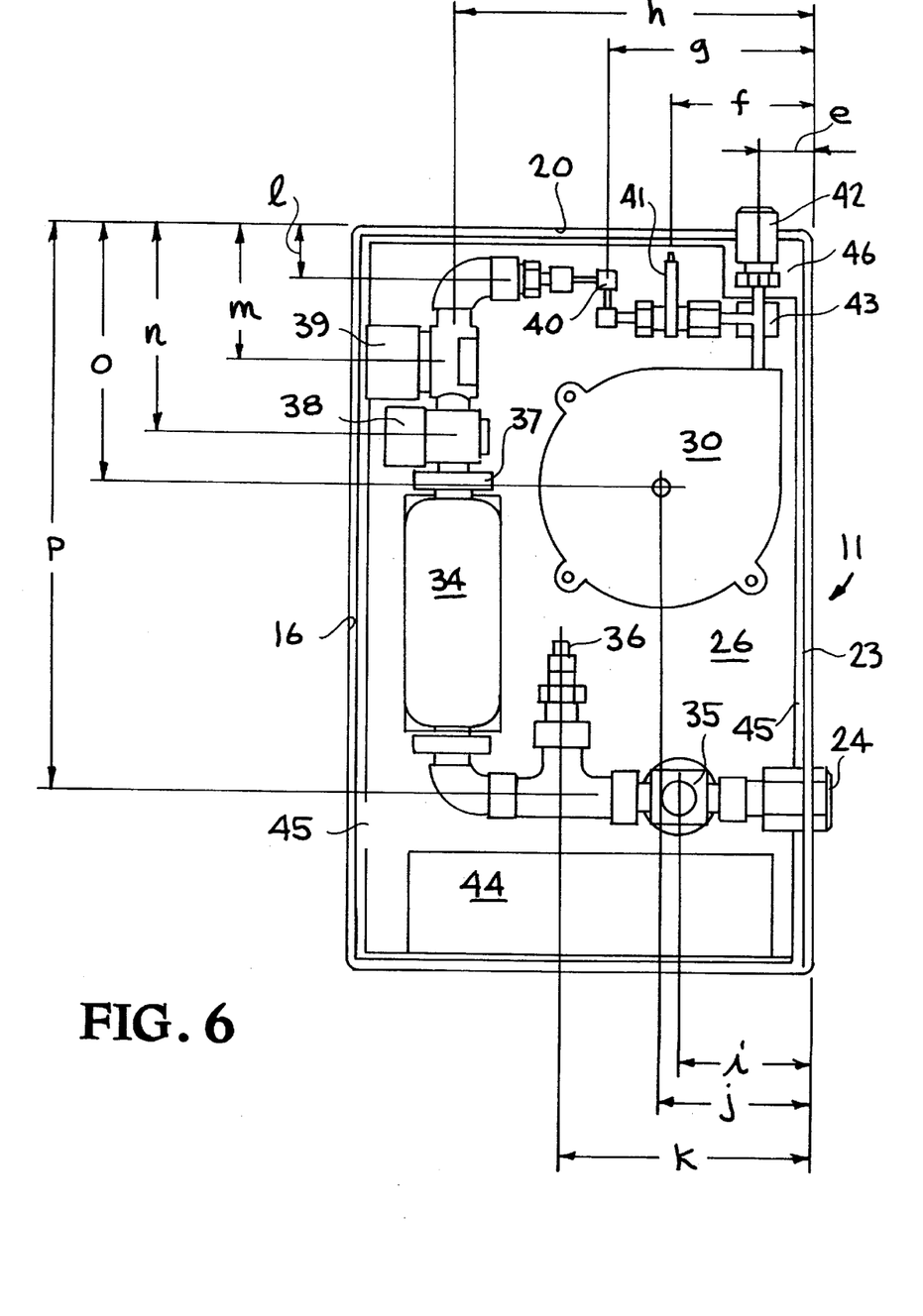
FIG. 6 is a top view of the multiple GC system of FIG. 5, showing dimensions of the various components to illustrate the compact size of the multiple GC system of the invention.

FIG. 5 illustrates the lower carrier section 11 of the carrier 10 of FIGS. 1–4 and corresponding components are given like reference numerals. Mounted within lower carrier section 11 are the major components of the system including a stack of four gas chromatograph columns 30, 31, 32 and 33, a gas storage bottle 34, such as a 40 cc bottle, an on/off valve 35, a pressure relief valve 36, a pair of mounting blocks 37, an on/off valve 38, a regulator 39, a gas (He) inlet divider 40, a pair of pressure sensors 41, at least one sample injector 42, and a mount 43, along with various interconnecting hardware. Thus, within the carrier lower section 11, is mounted a multiple GC system, wherein each of GCs columns 30–33 operates independently and can operate simultaneously. As shown in FIG. 6, a battery pack 44 is mounted in the lower carrier section 11 and which may comprise a power source which is sufficient to operate the components carried within carrier 10, including the computer 13.

To further illustrate the miniaturization and compact-size of the multiple GC system of the present invention. FIG. 6 shows various numerical distances between components as follows:

From the outer surface of the rear section 23 of lower section 11, are the distances to the center of sample injector 42 indicated by arrow e as 0.780 inch, to the pressure sensor 41 indicated by arrow f as 1.946 inches, to the He inlet divider 40 indicated by arrow g as 2.796 inches, to the center of the gas storage bottle 34 indicated by arrow h as 4.858 inches, to the center of on/off valve 35 indicated by arrow i as 1.797 inches, to the center of GC column 30 indicated arrow j as 2.053 inches, and to the center of pressure relief valve 36 indicated by arrow k as 3.372 inches. From the outer surface of the side section 20 of lower carrier section 11, are the distances to the center of He inlet divider 40 indicated by arrow 1 as 0.715 inch, to the center of regulator 39 as indicated by arrow m as 1.865 inches, to the center of on/off valve 38 indicated arrow n as 2.885 inches, to the center of GC column 30 indicated by arrow o as 3.580 inches, and to the center of on/off valve 35 indicated by arrow p as 7.833 inches. FIG. 6 also shows an insulator layer indicated at 45 adjacent the wall sections 16, 20 and 23 of inner carrier section 11, and which includes an enlarged section 46 located about the sample injector 42.

Figure 7:
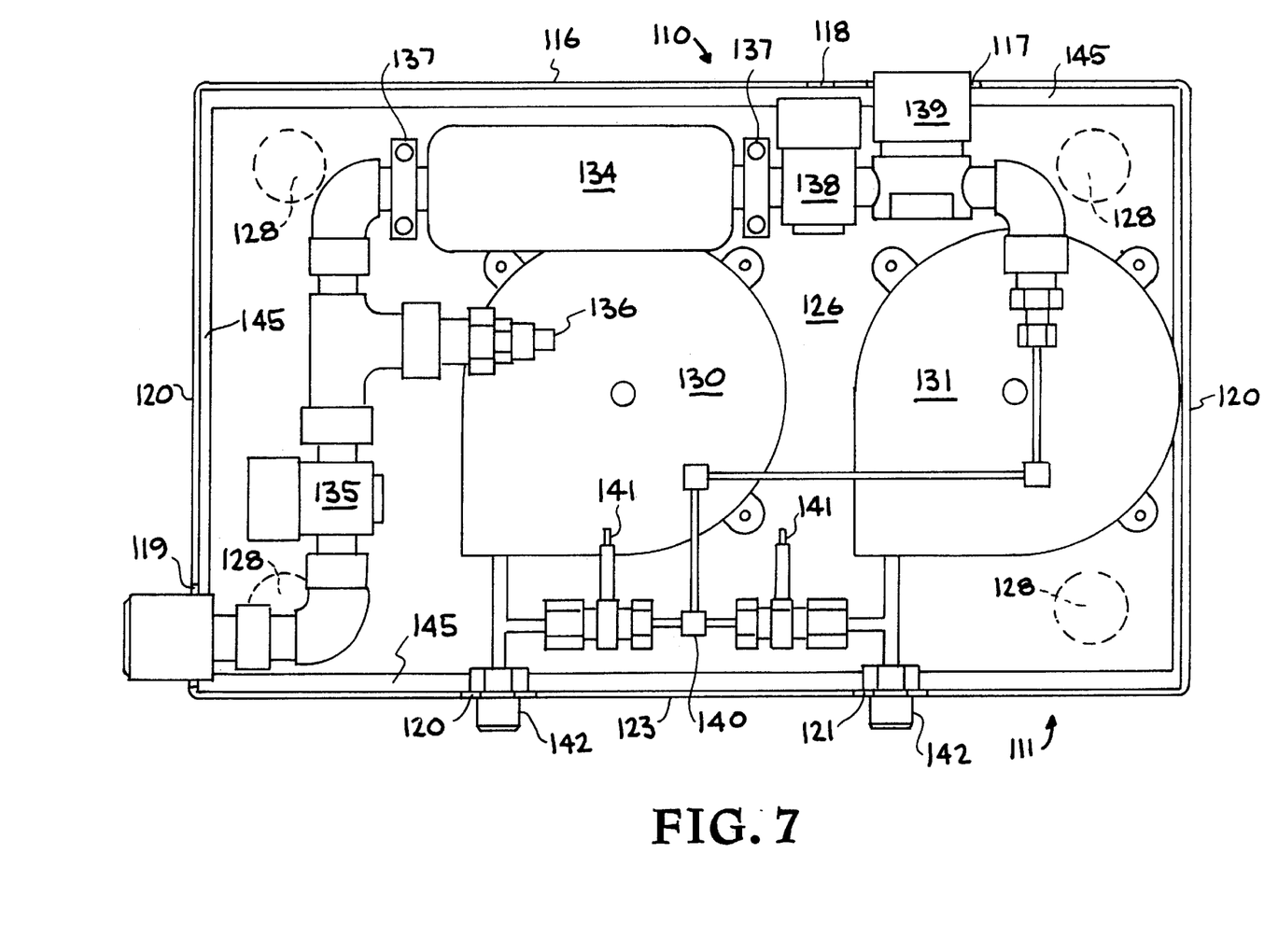
FIG. 7 is a top view of another embodiment of the hand-held multiple GC system of the invention, wherein the individual GCs are located in separate areas of the carrier.

FIG. 7 illustrates a larger embodiment of the hand-held multiple system GC incorporating the components of the present invention and utilizing two (2) stacks of independent GCs. As seen in FIG. 7 a hand-held GC carrier 110 includes a lower carrier section 111 having a front wall section 116, side wall sections 120, rear wall section 123, and bottom section 126. The lower carrier section 111 is provided with openings located similarly to the openings in lower carrier section 11 of FIGS. 1–6, and indicated at 117, 118 and 119 and additionally includes openings 120 and 121. Also, bottom section 126 is provided with support pads 128. While not shown, a battery pack is located in lower carrier section 111, as in FIG. 6. Within the lower carrier section 111 are positioned two (2) stacks of GC columns 130 and 131, each stack may be provided with a number of individual GS's as in FIG. 5, a gas storage bottle 134, an on/off valve 135, a pressure relief valve 136, a pair of mounting blocks 137, and on/off valve 138, a regulator 139, an He inlet divider 140, a pair of pressure sensors 141, a pair of sample injectors 142, and an insulation layer 145, along with the component interconnecting hardware.

Figure 8:
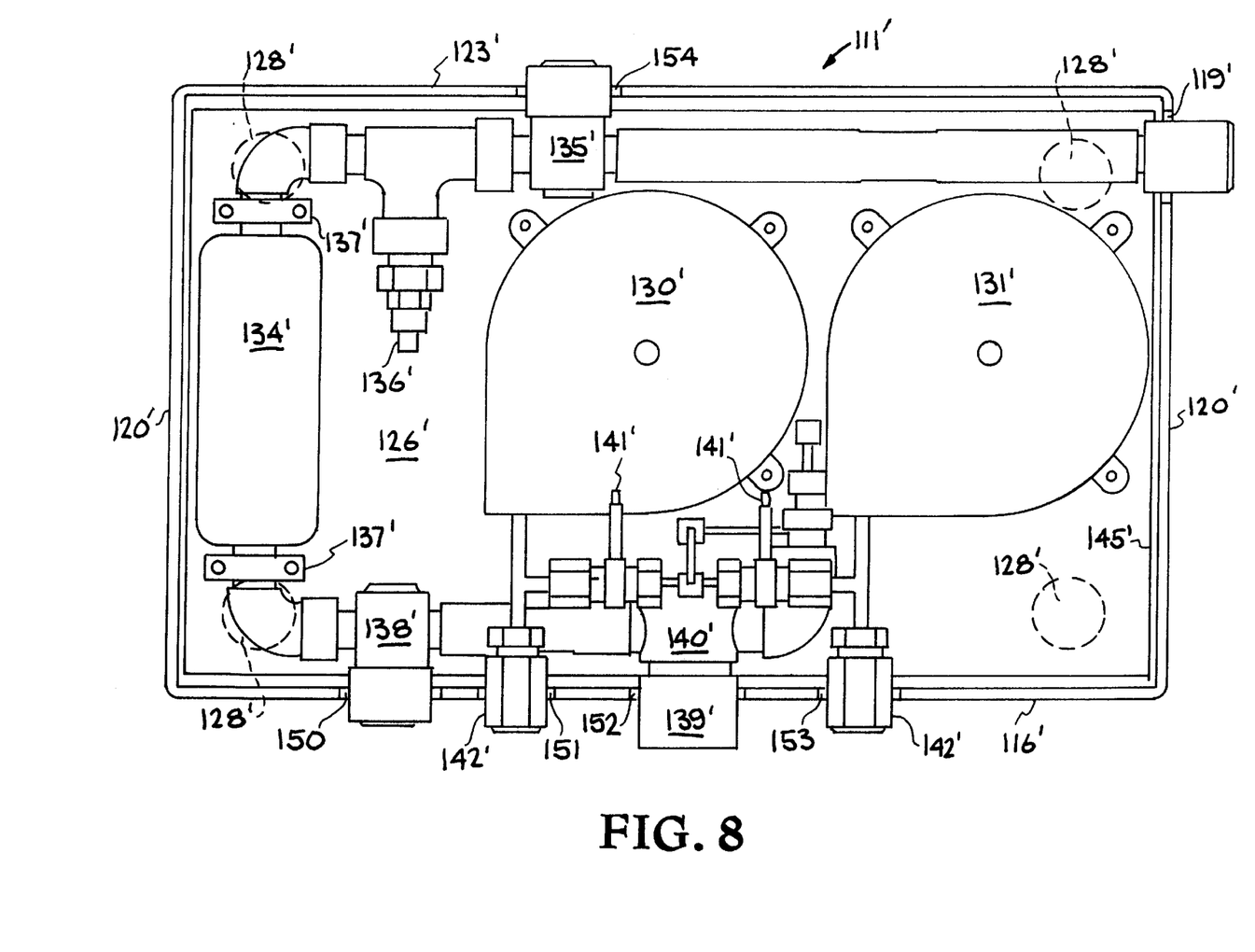
FIG. 8 is a top view of another embodiment of the hand-held multiple GC system, similar to FIG. 7, but with a different component arrangement within the carrier.

FIG. 8 illustrates another embodiment of a dual-stack GC hand-held system and the components thereof are relocated relative to the FIG. 7 embodiment, and similar components are given corresponding reference numerals. As seen in FIG. 8, a lower carrier section 111' includes wall section 116', 120' and 123' with a bottom section 126'. Wall section 116' is provided with openings 150, 151, 152 and 153, while wall section 123' is provided with an opening 119', while wall section 123' is provided with an opening 154, and bottom section 126' is provided with support pads 128'. Within lower carrier section 111' are two (2) stacks of GC columns 130' and 131', a gas supply bottle 134', and on/off valve 135', a pressure relief valve 136', a pair of mounting blocks 137', an on/off valve 138', a regulator 139', and He inlet divider 140', a pair of pressure sensors 141', a pair of sample injectors 142', an insulator layers 145', and associated interconnecting hardware with a battery pack not shown. The dimensions of the lower carrier section 111' may be the same as in the FIG. 7 embodiment.

It has thus been shown that the present invention provides a hand-held GC system which includes a plurality of individual GCs which operate independently and can operate simultaneously. The separation columns of the individual GCs may be provided with different coatings, whereby different retention times for the same gas will be measured. Thus, with multiple, parallel GCs, the system can measure, in a short time period, different retention times and provide a cross-reference in the determination of the measured gas and can become a two-dimensional system for direct field use for the detection of various chemical and biological substances.

While particular embodiments, parameters, etc. have been set forth to exemplify and explain the principles of the invention, such are not intended to be limiting. Modifications and changes may become apparent to those skilled in the art, and it is intended that the invention be limited only by the scope of the appended claims.

What is claimed is:

1. A multiple, parallel hand-held gas chromatograph system, including:
   a plurality of independent gas chromatographs,
   said plurality of independent gas chromatographs being mounted in a hand-held carrier.

2. The system of claim 1, wherein each of said independent gas chromatographs includes an injector, a separation column, a detector, and an oven.

3. The system of claim 1, wherein each of said plurality of gas chromatographs are constructed to operate independently and simultaneously.

4. The system of claim 1, wherein at least a portion of said plurality of independent gas chromatographs have separation columns with different coatings thereon, whereby different retention times for a gas passing therethrough are obtained.

5. The system of claim 1, wherein said plurality of independent gas chromatographs are mounted in at least one stack within said hand-held carrier.

6. The system of claim 1, wherein said hand-held carrier additionally contains at least a gas supply and a power supply.

7. The system of claim 6, wherein said hand-held carrier additionally contains a pair of on/off valves and a pressure relief valve operatively connected to said gas supply, and contains a regulator, a gas divider and at least one pressure sensor operatively mounted intermediate said gas supply and said plurality of independent gas chromatographs.

8. The system of claim 1, additionally including a computer mounted in said hand-held carrier.

9. The system of claim 8, wherein said hand-held carrier comprises a lower section and an upper section, wherein said computer is mounted in said upper section, and wherein said plurality of independent gas chromatographs are mounted in said lower section.

10. The system of claim 9, wherein said lower section of said hand-held carrier is provided with a plurality of openings to provide access to components located within said hand-held carrier and operatively connected to said plurality of independent gas chromatographs.

11. The system of claim 10, wherein said components accessible through said openings include on/off valves for a gas supply for said plurality of independent gas chromatographs, a regulator for said gas supply, and sample injectors for said independent gas chromatographs.

12. The system of claim 9, additionally including a power supply located in said lower section of said hand-held carrier for said computer and said plurality of independent gas chromatographs.

13. A hand-held gas chromatograph system comprising:
a carrier having mounted therein a plurality of independent gas chromatographs mounted in at least one stack, a computer, a gas supply for said gas chromatograph, a power supply for said computer and said stack of independent gas chromatographs, at least one on/off valve for said gas supply, a pressure relief valve and a regulator for said gas supply, a gas inlet divider for said gas supply, and at least one pressure sensor for the independent gas chromatographs.

14. The system of claim 13, wherein each of said independent gas chromatographs includes an injector, a separation column, detector, and oven.

15. The system of claim 14, wherein the separation columns of the different independent gas chromatographs include different coatings thereon.

16. The system of claim 15, wherein said at least one stack comprises a plurality of stacks and wherein said plurality of gas chromatographs are mounted in said plurality of stacks located within said carrier.

17. The system of claim 13, wherein said carrier comprises an upper section and a lower section, said computer being located in said upper section, and said plurality of gas chromatographs, said gas supply, said power supply, said at least one on/off valve, said pressure relief valve and said regulator, said gas inlet divider, and said at least one pressure sensor being located in said lower section of said carrier.

18. The system of claim 13, wherein said gas supply comprises a pressurized gas bottle mounted in said carrier.

19. The system of claim 13, wherein said power supply comprises a battery pack mounted in said carrier.

* * * * *